United States Patent
Krellner

(10) Patent No.: US 7,581,428 B2
(45) Date of Patent: Sep. 1, 2009

(54) SENSOR SYSTEM AND METHOD

(75) Inventor: Theodore J. Krellner, Emporium, PA (US)

(73) Assignee: General Electric Company, Schenectady, NY (US)

(*) Notice: Subject to any disclaimer, the term of this patent is extended or adjusted under 35 U.S.C. 154(b) by 184 days.

(21) Appl. No.: 11/608,258

(22) Filed: Dec. 8, 2006

(65) Prior Publication Data
US 2008/0134752 A1 Jun. 12, 2008

(51) Int. Cl.
*G01N 7/00* (2006.01)
(52) U.S. Cl. .................. 73/23.2; 73/1.02; 73/1.06; 73/23.31
(58) Field of Classification Search .............. 73/1.01, 73/1.02, 1.06, 23.2, 23.31, 31.05
See application file for complete search history.

(56) References Cited

U.S. PATENT DOCUMENTS

| 4,394,222 | A | | 7/1983 | Rohr |
| 5,386,373 | A | * | 1/1995 | Keeler et al. ............. 700/266 |
| 5,658,445 | A | | 8/1997 | Haefele et al. |
| 6,177,001 | B1 | * | 1/2001 | Meyer ...................... 205/784 |
| 2006/0042353 | A1 | * | 3/2006 | Marquis et al. ............ 73/23.2 |

FOREIGN PATENT DOCUMENTS

JP 57203843 A 12/1982

OTHER PUBLICATIONS

Atkinson et al., "A Low-Cost Oxzygen Sensor Fabricated as a Screen-Printed Semiconducotr Device Suitable for Unheted Operatioin at Ambient Temperatures" Sensors and Actuators B, vol. 47, 1998, pp. 171-180.*

* cited by examiner

*Primary Examiner*—Daniel S Larkin
(74) *Attorney, Agent, or Firm*—GE Global Patent Operation

(57) ABSTRACT

An oxygen analyzer system includes first and second internally calibrated sensors each for detecting oxygen levels, and a processing subsystem responsive to the sensors. The processor is configured to calibrate the first sensor while the second sensor detects oxygen levels, and to calibrate the second sensor while the first sensor detects oxygen levels. The processor is further configured to compare the oxygen level detected by the first internally calibrated oxygen sensor and the oxygen level detected by the second internally calibrated oxygen sensor, to output an error signal if the oxygen levels detected by the first internally calibrated sensor differ from the oxygen level detected by the second internally calibrated oxygen sensor by a predetermined amount, and to output the oxygen level detected by either the first or second internally calibrated oxygen sensor if the oxygen levels detected thereby do not differ by a predetermined amount.

32 Claims, 4 Drawing Sheets

SENSOR SYSTEM AND METHOD

FIELD OF THE INVENTION

This subject invention relates to sensors including internally calibrated oxygen sensors.

BACKGROUND OF THE INVENTION

Various types of measuring instruments, meters and analyzers utilize sensors to measure a variety of parameters. In one example, flue gas from combustion processes is analyzed by an oxygen analyzer to detect the presence of oxygen to give an indication of the efficiency of process heaters, oil burner systems, utility boilers, and the like. An accurate analysis can minimize fuel costs and reduce pollution while increasing safety.

Such measuring devices require periodic calibration to maintain accuracy. In some instruments, a known gas is piped in through a calibration port and the instrument is adjusted in accordance with this known reference gas. In other devices, the requirement of a reference gas may be eliminated. One such device is a General Electric OxyTrak 411 Flue Gas Oxygen Analyzer, which includes an internally calibrated sensor, the subject of U.S. Pat. No. 6,177,001, incorporated herein by this reference.

In any system, however, minimizing or eliminating costly down time for calibration is highly desirable. If, for example, a self-calibrating analyzer takes fifteen minutes to calibrate, then during that fifteen minutes, no analysis is performed and data such as the oxygen level of the flue gas is not recorded.

SUMMARY OF THE INVENTION

Embodiments of this invention provide a cost-effective, less complex, more robust and reliable sensing system and method capable of continuous gathering of pertinent data (e.g. the level of oxygen present in a gaseous environment) while still maintaining accuracy. System downtime is minimized or eliminated. Such a result is achieved by periodic and redundant calibration utilizing one sensor to gather data while the other sensor is calibrated.

In the various embodiments of this invention, the applicant's calibration system and method includes at least two sensors for detecting a parameter such as oxygen levels in a gaseous environment. At separate periodic intervals, each sensor is calibrated such that, at all times, at least one sensor is detecting the parameter.

The invention embodiments, however, need not achieve all these objectives and results and the claims hereof should not be limited to structures or methods capable of achieving these objectives and results.

This invention features an oxygen analyzer system including a first internally calibrated sensor for detecting oxygen levels, at least a second internally calibrated sensor for detecting oxygen levels, and a processing subsystem responsive to both the first and second internally calibrated sensors. The processing subsystem is configured to calibrate the first internally calibrated sensor while the second internally calibrated sensor detects the oxygen levels, calibrate the second internally calibrated sensor while the first internally calibrated sensor detects the oxygen levels, and compare the oxygen level detected by the first internally calibrated oxygen sensor and the oxygen level detected by the second internally calibrated oxygen sensor. If the oxygen levels detected by the first internally calibrated sensor differs from the oxygen levels detected by the second internally calibrated sensor by a predetermined amount, the processing subsystem is configured to output an error signal, and to output the oxygen level detected by either the first or second internally calibrated oxygen sensor if the oxygen levels detected thereby do not differ by a predetermined amount.

In one embodiment the first and second internally calibrated sensors each include a zirconium oxide wall forming an empty shell about a close chamber and having an inner face and an outer face, the inner face and outer face having an inner and an outer porous conductive coating, respectively, effective for establishing inner and outer equipotential surfaces at the inner and the outer faces. A conductor passes externally of said closed empty chamber and connecting to the inner face to electrically communicate therewith and thus to register or to define a difference in oxygen level across the thickness dimension of the shell. The zirconium oxide wall and porous conductive coatings are configured to effectively pump oxygen across the wall to track changing oxygen concentration in a sample of unknown concentration being measured whereby by applying charge to the electrodes the shell operates as an electrochemical pump and by detecting potential across the electrodes the shell operates as a Nernst cell for effective calibration and measurement of oxygen level at the outside surface. The first and second internally calibrated sensors may also simultaneously detect oxygen levels.

In one variation, there is a housing about the first and second internally calibrated sensors, and in another variation, there is a first housing about the first internally calibrated oxygen sensor and a second housing about the second internally calibrated sensor.

This invention also features a sensor system including a first sensor for detecting a parameter, at least a second sensor for detecting the same parameter, and a processing subsystem responsive to both the first and second sensors. The processing subsystem is configured to calibrate the first sensor while the second sensor detects the parameter, calibrate the second sensor while the first sensor detects the parameter, and output a reading corresponding to detection of the parameter. In one example the processing subsystem is further configured to output an error signal if output of the first sensor differs from output of the second sensor by a predetermined amount. The first and second sensors may be self-calibrating sensors and/or the first and second sensors may be internally calibrated oxygen sensors. In one variation, the first and second internally calibrated oxygen sensors each include a zirconium oxide wall forming an empty shell about a close chamber and having an inner face and an outer face, the inner face and outer face having an inner and an outer porous conductive coating, respectively, effective for establishing inner and outer equipotential surfaces at the inner and the outer faces. A conductor passes externally of said closed empty chamber and connecting to the inner face to electrically communicate therewith and thus to register or to define a difference in oxygen level across the thickness dimension of the shell. The zirconium oxide wall and porous conductive coatings are configured to effectively pump oxygen across the wall to track changing oxygen concentration in a sample of unknown concentration being measured whereby by applying charge to the electrodes the shell operates as an electrochemical pump and by detecting potential across the electrodes the shell operates as a Nernst cell for effective calibration and measurement of oxygen level at the outside surface.

In one embodiment, there is a housing about the first and second sensors, and in another embodiment there is a first housing about the first sensor and a second housing about the second sensor. The first and second sensors may simultaneously detect the parameter, e.g. oxygen levels.

This invention further features a sensor system including a first oxygen sensor for detecting oxygen levels in a selected environment, at least a second oxygen sensor for detecting the oxygen levels, and a processing subsystem responsive to both the first and second oxygen sensors. The processing subsystem is configured to calibrate the first oxygen sensor while the second oxygen sensor detects the oxygen levels, calibrate the second oxygen sensor while the first oxygen sensor detects the oxygen levels, and output a reading corresponding to detection of the oxygen levels. In one example the processing subsystem is further configured to output an error signal if oxygen levels detected by the first oxygen sensor differ from oxygen levels detected by the second oxygen sensor by a predetermined amount. There may be a housing about the first and second oxygen sensors, and/or there may be a first housing about the first oxygen sensor and a second housing about the second oxygen sensor. The first and second oxygen sensors may simultaneously detect the oxygen levels, and the first and second oxygen sensors may be self-calibrating sensors.

This invention also features a sensing method for a system including at least first and second internally calibrated oxygen sensors, the method including calibrating the first internally calibrated oxygen sensor at periodic intervals, and while the first internally calibrated oxygen sensor is being calibrated, using the second internally calibrated oxygen sensor to detect oxygen levels, calibrating the second internally calibrated sensor at periodic intervals, and while the second internally calibrated oxygen sensor is being calibrated, using the first internally calibrated oxygen sensor to detect oxygen levels. In one embodiment the method includes comparing the oxygen levels detected by the first and second internally calibrated sensors and outputting an error signal if the oxygen levels detected by the first internally calibrated sensor differ from the oxygen levels detected by the second internally calibrated sensor by a predetermined amount. In one variation, the method includes outputting oxygen levels detected by either the first or second internally calibrated oxygen sensor if the oxygen levels detected thereby do not differ by a predetermined amount. The method may also include the first and second internally calibrated sensors simultaneously detecting oxygen levels, and/or disposing a housing about the first and second internally calibrated sensors or disposing a first housing about the first internally calibrated sensor and a second housing about the second internally calibrated sensor.

This invention further features a sensing method for a system including at least first and second sensors, the method including calibrating the first sensor at periodic intervals and while the first sensor is being calibrated, using the second sensor to detect a parameter, calibrating the second sensor at periodic intervals, and while the second sensor is being calibrated, using the first sensor to detect the parameter. In one embodiment the method also includes comparing outputs of the first and second sensors and outputting an error signal if the output of the first sensor differs from the output of the second sensor by a predetermined amount. In one variation, the method includes outputting the parameters detected by either the first or second sensor if the parameters detected thereby do not differ by a predetermined amount. The method may also include the first and second sensors simultaneously detecting the parameter, and the first and second sensors may be self-calibrating sensors. The method may further include disposing a housing about the first and second sensors, or disposing a first housing about the first sensor and a second housing about the second sensor.

This invention also features a sensing method for a system including at least first and second oxygen sensors, the method including calibrating the first oxygen sensor at periodic intervals and while the first oxygen sensor is being calibrated, using the second oxygen sensor to detect oxygen levels, calibrating the second oxygen sensor at periodic intervals, and while the second oxygen sensor is being calibrated, using the first oxygen sensor to detect oxygen levels. In one example the method includes comparing the oxygen levels detected by the first and second oxygen sensors and outputting an error signal if the oxygen levels detected by the first oxygen sensor differ from the oxygen level detected by the second oxygen sensor by a predetermined amount. In one variation, the method includes outputting the oxygen levels detected by either the first or second oxygen sensor if the oxygen levels detected thereby do not differ by predetermined amount. The first and second oxygen sensors may simultaneously detect oxygen levels. In one variation the first and second oxygen sensors are self-calibrating oxygen sensors. The method may also include disposing a housing about the first and second oxygen sensors, or disposing a first housing about the first oxygen sensor and a second housing about the second oxygen sensor.

BRIEF DESCRIPTION OF THE SEVERAL VIEWS OF THE DRAWINGS

Other objects, features and advantages will occur to those skilled in the art from the following description of a preferred embodiment and the accompanying drawings, in which.

DETAILED DESCRIPTION OF THE INVENTION

Figure 1:
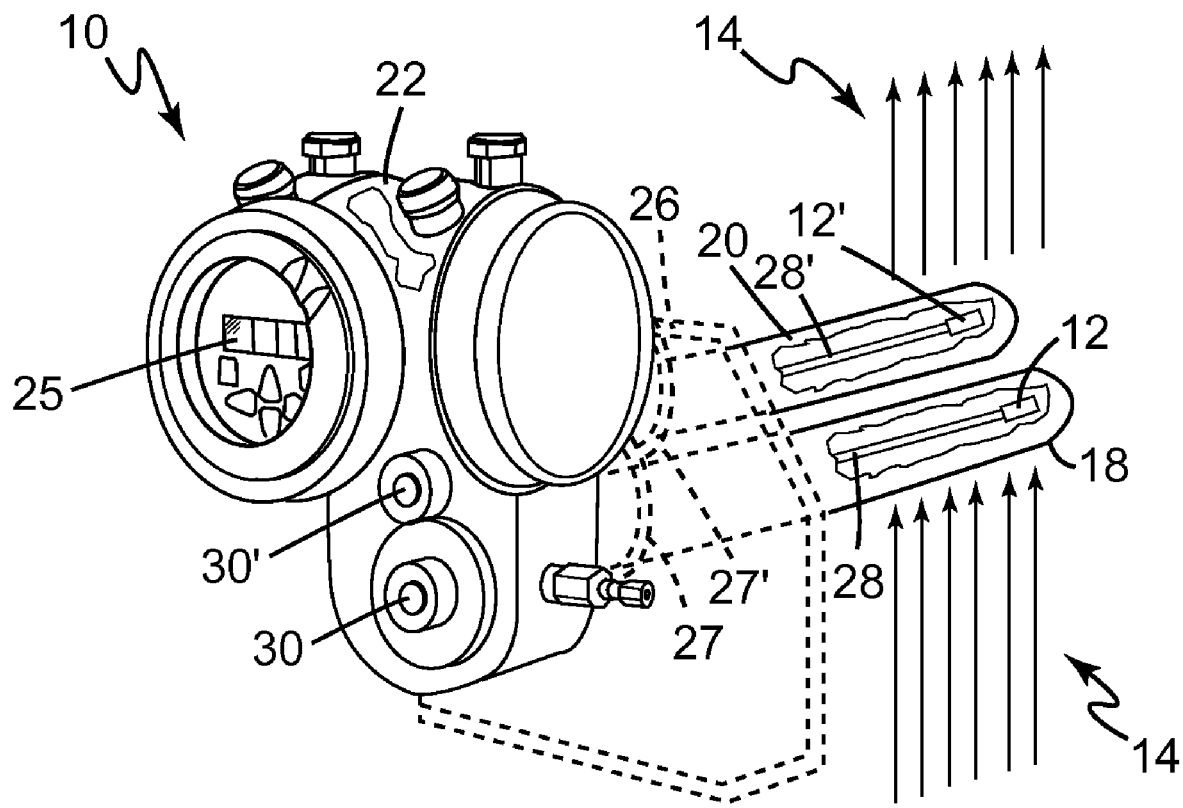
FIG. 1 is a schematic three-dimensional partial cutaway view showing one example of a system in accordance with the present invention.

Aside from the embodiment or embodiments disclosed below, this invention is capable of other embodiments and of being practiced or being carried out in various ways. Thus, it is to be understood that the invention is not limited in its application to the details of construction and the arrangements of components set forth in the following description or illustrated in the drawings. If only one embodiment is described herein, the claims hereof are not to be limited to that embodiment. Moreover, the claims hereof are not to be read restrictively unless there is clear and convincing evidence manifesting a certain exclusion, restriction, or disclaimer.

In the field of combustion processes, increasing the efficiency of a burner or boiler system can save fuel costs. The age of the system, variations in fuel mixtures and types of fuels, and even weather conditions may adversely affect the system's efficiency. In order to make improvements, however, there needs to be a way to assess the effectiveness of the system in the first instance. In many cases such assessments require the system to be shut down, and thus decrease productivity. The subject invention provides an alternative to either operating an inefficient system or shutting the system down.

In one embodiment of the subject invention, sensor system 10, FIG. 1 includes internally calibrated sensor 12 for detecting the oxygen levels in flue gas 14 flowing from a burner or other combustion system. At least one other internally calibrated sensor 12' also detects oxygen levels in flue gas 14. An electronics subsystem typically including a processor within housing 22 is responsive to both internally calibrated sensors 12 and 12', and is configured to calibrate sensor 12 while sensor 12' detects oxygen levels, and, alternately, to calibrate sensor 12' while sensor 12 detects oxygen levels. Sensors 12 and 12' are calibrated at periodic intervals as desired. Typically, during periods when there is no calibration, sensors 12 and 12' both read oxygen levels, although this is not necessary, and one sensor can be used during times when there is no calibration. System 10 thus provides the advantage of periodic calibration to maintain system accuracy, yet there is at least one sensor detecting oxygen levels at all times, thus eliminating downtime for calibration.

Although there may be some minor differences in the oxygen levels detected by sensors 12 and 12' by virtue of their relative positions in flue gas 14, in most cases the oxygen level read by sensors 12 and 12' should be virtually the same, since both sensors are measuring the same flue gas 14 from the same combustion process. For redundancy and as an additional check for system accuracy, however, in one embodiment the processor is configured such that it outputs an error signal if the oxygen levels detected by sensors 12 and 12' differ by a predetermined amount. The predetermined amount can be tailored as desired, e.g. according to the type of combustion system monitored. With the data received from sensors 12 and 12', the processor outputs a reading on display 25, in this example oxygen level, which may be viewed by the system operator.

Figure 5:
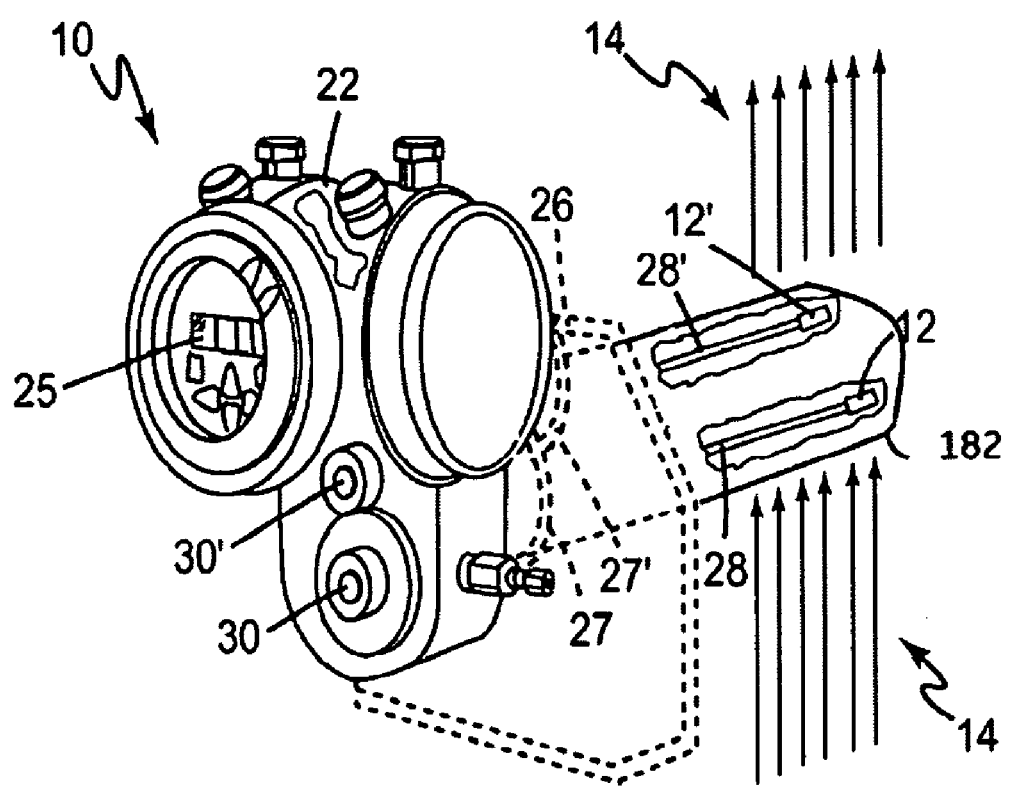
FIG. 5 is a schematic three-dimensional partial cutaway view showing another example of a system in accordance with the present invention.

In one aspect of the invention, housing 18 is disposed about internally calibrated sensor 12 and housing 20 about sensor 12'. In another variation, sensors 12 and 12' may both be contained within a single housing 182 (FIG. 5). In the example pertaining to measurement of oxygen levels in flue gases, system 10 may be attached to and pass through flue wall 26 via mating flanges 27 and 27', for example, and sensors 12 and 12' may include probe sections 28 and 28' and be inserted through access ports 30 and 30' similar to the design of the GE Sensing OxyTrak® 411 Flue Gas Oxygen Analyzer.

Figure 2:
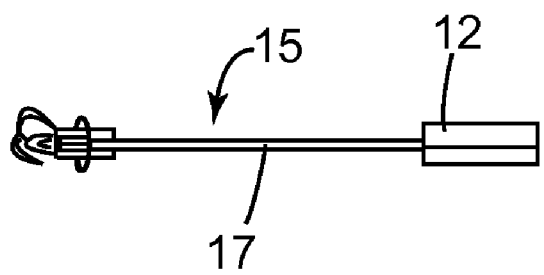
FIG. 2 is a schematic side view showing one example of a sensor assembly for use with the present invention.
Figure 3:
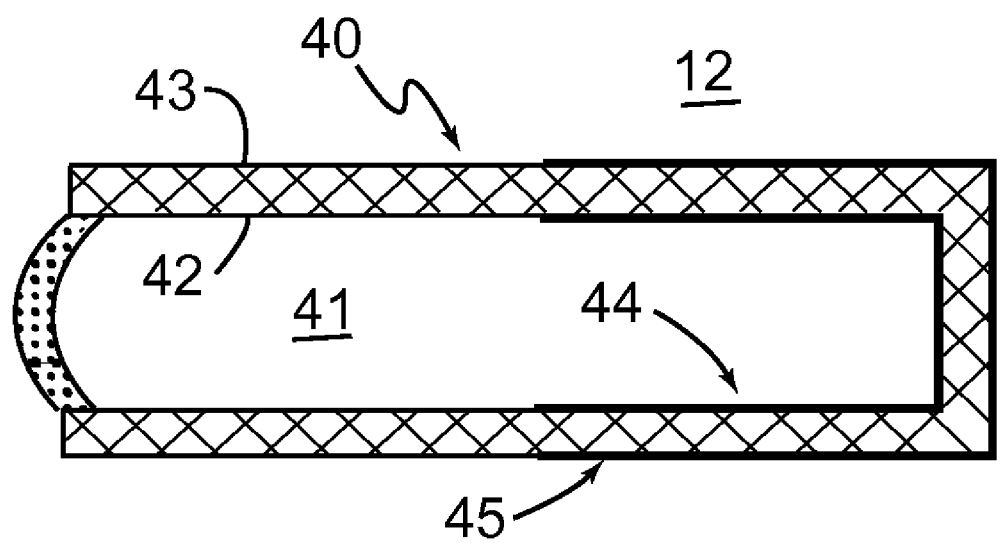
FIG. 3 is a highly schematic cross-sectional view of the sensor of FIG. 2.

In one embodiment, sensors 12 and 12' are internally calibrated oxygen sensors of the type utilized with the GE Sensing OxyTrak® 411 Flue Gas Oxygen Analyzer, and/or disclosed in U.S. Pat. No. 6,177,001, which is incorporated herein by reference. In such an embodiment, sensors 12 and 12' include sensor assembly 15, FIG. 2, probe 17. Sensors 12 and 12' are each self-calibrating zirconium oxide oxygen sensors, and include a sealed internal reference chamber. Sensors 12 and 12' include zirconium oxide wall 40, FIG. 3 forming an empty shell about closed chamber 41 and having inner face 42 and outer face 43. Inner face 42 and outer face 43 have an inner and an outer porous conductive coating, respectively, effective for establishing inner and outer equipotential surfaces at the inner and the outer faces, and a conductor (not shown) passing externally of closed empty chamber 41 and connecting to inner face 42 to electrically communicate therewith and thus to register or to define a difference in oxygen level across the thickness dimension of the shell. Zirconium oxide wall 40 and porous conductive coatings are configured to effectively pump oxygen across the wall to track changing oxygen concentration in a sample of unknown concentration being measured whereby by applying charge to the electrodes the shell operates as an electrochemical pump. By detecting potential across electrodes 44 and 45 the shell operates as a Nernst cell for effective calibration and measurement of oxygen level at the outside surface.

In other embodiments, sensors 12 and 12', FIG. 1, do not necessarily need to be identical sensors, nor must one or both be internally calibrated. System 10 may be used in conjunction with detection of any type of desired parameter or gathering of any type of data, and is not limited to detection of oxygen in flue gas or associated with combustion systems. Sensors 12 and 12' may each be placed in any selected environment—such as a gaseous environment in one example—with each detecting a parameter in that selected environment. In these embodiments, processor 22 is also responsive to sensors 12 and 12', and configured to calibrate sensor 12 while sensor 12' is detecting the desired parameter, and to calibrate sensor 12' while sensor 12 is detecting the same parameter. In one variation, the parameter to be determined is oxygen level and the sensors are oxygen sensors, and/or the sensors are self-calibrating. Additionally, in these embodiments there are also times of no calibration, when sensors 12 and 12' are both measuring or detecting some parameter, and processor 22 is configured as described herein, to be responsive to any type of sensors and to output a reading. Also, for example when a parameter, e.g. oxygen level, detected by sensor 12 differs substantially from the same parameter detected by sensor 12', processor 22 outputs an error signal.

Another aspect, the sensor system 10, is shown in FIG. 5, comprising a single housing 182 disposed about internally calibrated sensors 12 and 12'.

Other embodiments of systems in accordance with the present invention include but are not limited to various combinations of types of sensors (e.g. internally calibrated sensors, self-calibrating sensors, oxygen sensors or other types of sensors), which can be calibrated at various periodic intervals and placed in diverse selected environments (e.g. gaseous environments or flue gas), for detecting and outputting a reading for any number of parameters (e.g. oxygen levels), which result from combustion or any other process to be monitored. It is clear then that in its various embodiments, the subject invention provides system flexibility, increased accuracy, and cost savings.

Figure 4:
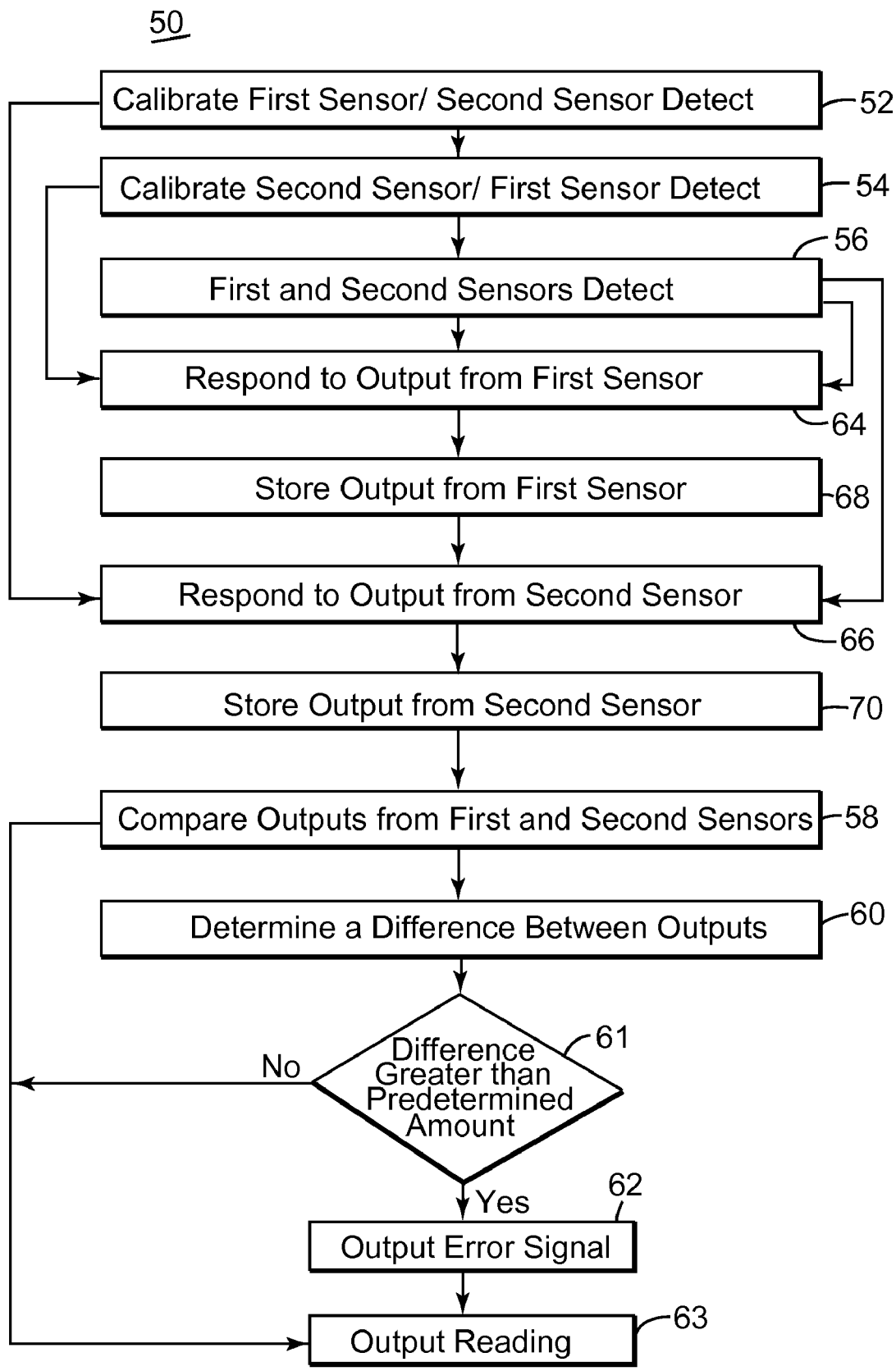
FIG. 4 is a flowchart depicting the primary steps associated with one example of the programming of the electronics subsystem for the subject invention.

One embodiment of a sensing method 50, FIG. 4 in accordance with the subject invention includes disposing at least two sensors in a selected environment. The processing circuitry responsive to and controlling both sensors is configured to calibrate one (e.g., a first) sensor at periodic intervals (e.g., once a day) while at least one other (e.g., a second) sensor detects or measures a parameter, step 52. Once the first sensor finishes calibration, the second sensor is then calibrated (also, for example, once a day) and now the first sensor is detecting, step 54. In one typical example, during times when no sensor is being calibrated, both sensors (e.g., the first and second sensors) detect or measure, step 56, although this is not necessary, and only one sensor may detect or measure a parameter during times when there is no calibration. Accordingly, with this sensing method accuracy is achieved by timely sensor calibration, and greater production is achieved by reducing or eliminating downtime for sensor calibration. For even greater accuracy, in one variation the method further includes comparing outputs of the first and second sensors, step 58, determining a difference between outputs, step 60, and if the difference is greater than a predetermined amount, step 61, outputting an error signal, step 62. If the difference is less than the predetermined amount a measurement reading, for example, is output, step 63. Typically, the sensing method includes responding to output from the first and second sensors, steps 64 and 66, and optionally storing the sensor outputs, steps 68 and 70.

Other method embodiments in accordance with the present invention include any number of combinations of the steps of FIG. 4, with any combination of types of sensors, types of parameters to be detected and/or measured, in any chosen environment.

As with the embodiments of the system of the subject invention, method embodiments may include but are not limited to combinations of sensors (e.g. internally calibrated sensors, self-calibrating sensors, oxygen sensors or other types of sensors), which can be calibrated at various periodic intervals and placed in diverse selected environments (e.g. gaseous environments or flue gas), for detecting and outputting a reading for any number of parameters (e.g. oxygen levels), which result from combustion or any other process to be monitored.

Accordingly, the various embodiments of the present invention provide an economical sensing system and method which is capable of continuous gathering of data while maintaining accuracy, minimizing or eliminating system downtime, and increasing cost-effectiveness.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

Although specific features of the invention are shown in some drawings and not in others, this is for convenience only as each feature may be combined with any or all of the other features in accordance with the invention. The words "including", "comprising", "having", and "with" as used herein are to be interpreted broadly and comprehensively and are not limited to any physical interconnection. Moreover, any embodiments disclosed in the subject application are not to be taken as the only possible embodiments. Other embodiments will occur to those skilled in the art and are within the following claims.

In addition, any amendment presented during the prosecution of the patent application for this patent is not a disclaimer of any claim element presented in the application as filed. Those skilled in the art cannot reasonably be expected to draft a claim that would literally encompass all possible equivalents, many equivalents will be unforeseeable at the time of the amendment and are beyond a fair interpretation of what is to be surrendered (if anything), the rationale underlying the amendment may bear no more than a tangential relation to many equivalents, and/or there are many other reasons the applicant can not be expected to describe certain insubstantial substitutes for any claim element amended.

What is claimed is:

1. An oxygen analyzer system comprising:
    a first internally calibrated sensor for detecting oxygen levels;
    at least a second internally calibrated sensor for detecting oxygen levels; and
    a processing subsystem responsive to both the first and second internally calibrated sensors and configured to:
        calibrate the first internally calibrated sensor while the second internally calibrated sensor detects the oxygen levels;
        calibrate the second internally calibrated sensor while the first internally calibrated sensor detects the oxygen levels;
        compare the oxygen level detected by the first internally calibrated oxygen sensor and the oxygen level detected by the second internally calibrated oxygen sensor;
        output an error signal if the oxygen levels detected by the first internally calibrated sensor differ from the oxygen levels detected by the second internally calibrated sensor by a predetermined amount; and
        output the oxygen level detected by either the first or second internally calibrated oxygen sensor if the oxygen levels detected thereby do not differ by a predetermined amount.

2. The system of claim 1 in which the first and second internally calibrated sensors each include a zirconium oxide wall forming an empty shell about a close chamber and having an inner face and an outer face, the inner face and outer face having an inner and an outer porous conductive coating, respectively, effective for establishing inner and outer equipotential surfaces at the inner and the outer faces, and a conductor passing externally of said closed empty chamber and connecting to the inner face to electrically communicate therewith and thus to register or to define a difference in oxygen level across the thickness dimension of the shell, the zirconium oxide wall and porous conductive coatings configured to effectively pump oxygen across the wall to track changing oxygen concentration in a sample of unknown concentration being measured whereby by applying charge to the electrodes the shell operates as an electrochemical pump and by detecting potential across the electrodes the shell operates as a Nernst cell for effective calibration and measurement of oxygen level at the outside surface.

3. The system of claim 1 in which the first and second internally calibrated sensors simultaneously detect oxygen levels.

4. The system of claim 1 including a housing about the first and second internally calibrated sensors.

5. The system of claim 1 including a first housing about the first internally calibrated oxygen sensor and a second housing about the second internally calibrated sensor.

6. A sensor system comprising:
    a first sensor for detecting a parameter;
    at least a second sensor for detecting the same parameter; and
    a processing subsystem responsive to both the first and second sensors and configured to:
        calibrate the first sensor while the second sensor detects the parameter;
        calibrate the second sensor while the first sensor detects the parameter; and
        output a reading corresponding to detection of the parameter; and
        output an error signal if an output of the first sensor differs from an output of the second sensor by a predetermined amount.

7. The system of claim 6 in which the first and second sensors are self-calibrating sensors.

8. The system of claim 6 in which the first and second sensors are internally calibrated oxygen sensors.

9. The system of claim 8 in which the first and second internally calibrated oxygen sensors each include a zirconium oxide wall forming an empty shell about a close chamber and having an inner face and an outer face, the inner face and outer face having an inner and an outer porous conductive coating, respectively, effective for establishing inner and outer equipotential surfaces at the inner and the outer faces, and a conductor passing externally of said closed empty chamber and connecting to the inner face to electrically communicate therewith and thus to register or to define a difference in oxygen level across the thickness dimension of the shell, the zirconium oxide wall and porous conductive coatings configured to effectively pump oxygen across the wall to track changing oxygen concentration in a sample of unknown concentration being measured whereby by applying charge to the electrodes the shell operates as an electrochemical pump and by detecting potential across the electrodes the shell operates as a Nernst cell for effective calibration and measurement of oxygen level at the outside surface.

10. The system of claim 6 including a housing about the first and second sensors.

11. The system of claim 6 in which the first and second sensors simultaneously detect the parameter.

12. A sensor system comprising:
   a first oxygen sensor for detecting oxygen levels in a selected environment;
   at least a second oxygen sensor for detecting the oxygen levels; and
   a processing subsystem responsive to both the first and second oxygen sensors and configured to:
      calibrate the first oxygen sensor while the second oxygen sensor detects the oxygen levels;
      calibrate the second oxygen sensor while the first oxygen sensor detects the oxygen levels; and
      output a reading corresponding to detection of the oxygen levels; and
      output an error signal if oxygen levels detected by the first oxygen sensor differ from oxygen levels detected by the second oxygen sensor by a predetermined amount.

13. The system of claim 12 including a housing about the first and second oxygen sensors.

14. The system of claim 12 including a first housing about the first oxygen sensor and a second housing about the second oxygen sensor.

15. The system of claim 12 in which the first and second oxygen sensors simultaneously detect the oxygen levels.

16. The system of claim 12 in which the first and second oxygen sensors are self-calibrating sensors.

17. A sensor method for a system including at least first and second internally calibrated oxygen sensors, the method comprising:
   calibrating the first internally calibrated oxygen sensor at periodic intervals;
   while the first internally calibrated oxygen sensor is being calibrated, using the second internally calibrated oxygen sensor to detect oxygen levels;
   calibrating the second internally calibrated sensor at periodic intervals; and
   while the second internally calibrated oxygen sensor is being calibrated, using the first internally calibrated oxygen sensor to detect oxygen levels; and
   comparing the oxygen levels detected by the first and second internally calibrated sensors and outputting an error signal if the oxygen levels detected by the first internally calibrated sensor differ from the oxygen levels detected by the second internally calibrated sensor by a predetermined amount.

18. The method of claim 17 further including outputting oxygen levels detected by either the first or second internally calibrated oxygen sensor if the oxygen levels detected thereby do not differ by a predetermined amount.

19. The method of claim 17 in which the first and second internally calibrated sensors simultaneously detect oxygen levels.

20. The method of claim 17 including disposing a housing about the first and second internally calibrated sensors.

21. The method of claim 17 including disposing a first housing about the first internally calibrated sensor and a second housing about the second internally calibrated sensor.

22. A sensing method for a system including at least first and second sensors, the method comprising:
   calibrating the first sensor at periodic intervals;
   while the first sensor is being calibrated, using the second sensor to detect a parameter;
   calibrating the second sensor at periodic intervals; and
   while the second sensor is being calibrated, using the first sensor to detect the parameter; and
   comparing outputs of the first and second sensors and outputting an error signal if the output of the first sensor differs from the output of the second sensor by a predetermined amount.

23. The method of claim 22 further including outputting the parameters detected by either the first or second sensor if the parameters detected thereby do not differ by a predetermined amount.

24. The method of claim 22 in which the first and second sensors simultaneously detect the parameter.

25. The method of claim 22 in which the first and second sensors are self-calibrating sensors.

26. The method of claim 22 including disposing a housing about the first and second sensors.

27. A sensing method for a system including at least first and second oxygen sensors, the method comprising:
   calibrating the first oxygen sensor at periodic intervals;
   while the first oxygen sensor is being calibrated, using the second oxygen sensor to detect oxygen levels;
   calibrating the second oxygen sensor at periodic intervals; and
   while the second oxygen sensor is being calibrated, using the first oxygen sensor to detect oxygen levels; and
   comparing the oxygen levels detected by the first and second oxygen sensors and outputting an error signal if the oxygen levels detected by the first oxygen sensor differ from the oxygen level detected by the second oxygen sensor by a predetermined amount.

28. The method of claim 27 further including outputting the oxygen levels detected by either the first or second oxygen sensor if the oxygen levels detected thereby do not differ by predetermined amount.

29. The method of claim 27 in which the first and second oxygen sensors simultaneously detect oxygen levels.

30. The method of claim 27 in which the first and second oxygen sensors are self-calibrating oxygen sensors.

31. The method of claim 27 including disposing a housing about the first and second oxygen sensors.

32. The method of claim 27 including disposing a first housing about the first oxygen sensor and a second housing about the second oxygen sensor.

* * * * *